(12) United States Patent
Spiess et al.

(10) Patent No.: US 6,846,803 B1
(45) Date of Patent: Jan. 25, 2005

(54) ANTAGONISTS SPECIFIC FOR THE CORTICOTROPIN-RELEASING FACTOR RECEPTOR TYPE 2 (CRFR2)

(75) Inventors: Joachim Spiess, Gottingen (DE); Andreas Ruhmann, Menai (AU)

(73) Assignee: Max Planck Gesellschaft zur Forderung der Wissenschaften E.V., Berlin (DE)

( * ) Notice: Subject to any disclaimer, the term of this patent is extended or adjusted under 35 U.S.C. 154(b) by 0 days.

(21) Appl. No.: 09/744,441

(22) PCT Filed: Jul. 23, 1999

(86) PCT No.: PCT/EP99/05297

§ 371 (c)(1),
(2), (4) Date: May 11, 2001

(87) PCT Pub. No.: WO00/05253

PCT Pub. Date: Feb. 3, 2000

(30) Foreign Application Priority Data

Jul. 24, 1998 (EP) .............................. 98113896

(51) Int. Cl.[7] .......................... A61K 38/16; C07K 14/00
(52) U.S. Cl. .......................... 514/12; 530/324; 530/345; 930/21
(58) Field of Search .............................. 930/21; 514/12; 530/324, 345

(56) References Cited

U.S. PATENT DOCUMENTS

| 4,474,765 A | | 10/1984 | de Castiglione et al. | |
| 5,464,757 A | * | 11/1995 | Potter et al. | ................ 435/69.1 |
| 5,874,227 A | * | 2/1999 | Rivier | ......................... 435/7.1 |

OTHER PUBLICATIONS

Lovenberg et al. Cloning and characterization of a functionally distinct corticotropin–releasing factor receptor subtype from rat brain. Proc Natl Acad Sci U S A. Jan. 31, 1995;92(3):836–40. Erratum in: Proc Natl Acad Sci U S A Jun. 6, 1995;92(12):5759.*

Gonzalez et al., Cell and Tissue Research, vol. 283, No. 1, pp. 117–123 (1996).
Gaudino et al., Peptides, vol. 6, Suppl. 3, pp. 209–213 (1985).
Lovenberg et al., Curr. Pharm. Des., vol. 1, No. 3, pp. 305–316 (1995).
Spiess et al., Trends Endocrinol. Metab., vol. 9, No. 4, pp. 140–145 (1998).
Behan et al., Mol. Psychiatry, vol. 1, No. 4, pp. 265–277 (1996).
Ruhmann et al., Proceeding of the Nat'l Acad. of Sciences of the USA, vol. 95, No. 26, pp. 15264–15269 (1998).

* cited by examiner

Primary Examiner—David Romeo
(74) Attorney, Agent, or Firm—Birch, Stewart, Kolasch & Birch, LLP

(57) ABSTRACT

The present invention relates to an antagonist of the ligand of the Corticotropin-Releasing Factor Receptor, type 2 (CRFR2) lacking the 8 to 10 N-terminal amino acids of native sauvagine. The present invention also relates to an antagonist of the ligand of the Corticotropin-Releasing Factor Receptor, type 2 (CRFR2) lacking the 11 N-terminal amino acids of native sauvagine, wherein the N-terminal amino acid of said antagonist is a charged amino acid. Furthermore, the present invention relates to a polynucleotide encoding the antagonist of the present invention, a vector comprising the polynucleotide of the present invention, and a host comprising the polynucleotide or the vector of the present invention. Also described are a method for producing the antagonist of the present invention, antibodies directed the antagonist of the present invention, as well as anti-idiotypic antibodies directed against the antibody of the present invention. The present invention also relates to pharmaceutical and diagnostic compositions comprising the antagonist, the polynucleotide, the vector, the antibody, and/or the anti-idiotypic antibody of the present invention. Furthermore, the present invention relates to a kit comprising one or more of the above mentioned compounds of the present invention and to the use of one or more of these compounds for the preparation of a pharmaceutical composition for preventing and/or treating a Corticotropin-Releasing Factor Receptor, type 2 (CRFR2)-associated disease.

20 Claims, 4 Drawing Sheets

Figure 1:
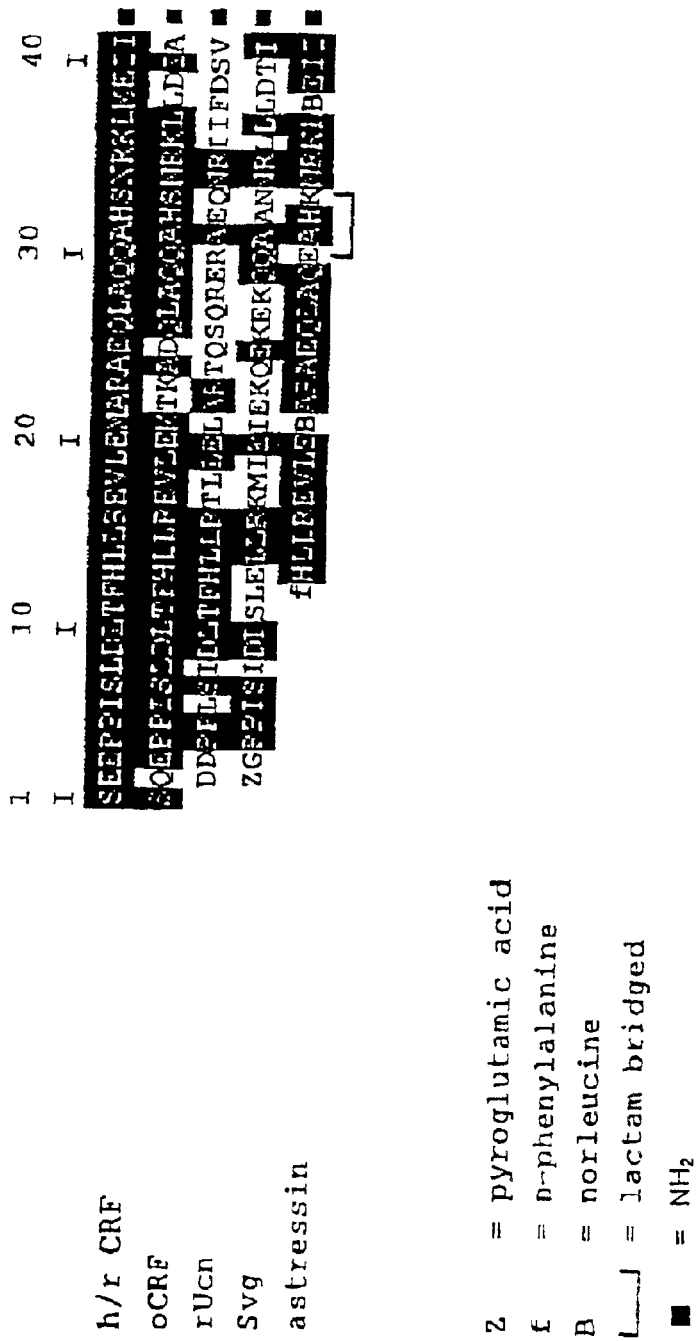

ANTAGONISTS SPECIFIC FOR THE CORTICOTROPIN-RELEASING FACTOR RECEPTOR TYPE 2 (CRFR2)

This application is the national phase under 35 U.S.C. § 371 of PCT International Application No. PCT/EP99/05297 which has an International filing date of Jul. 23, 1999, which designated the United States of America.

The present invention relates to an antagonist of the ligand of the Corticotropin-Releasing Factor Receptor, type 2 (CRFR2) lacking the 8 to 10 N-terminal amino acids of native sauvagine. The present invention also relates to an antagonist of the ligand of the Corticotropin-Releasing Factor Receptor, type 2 (CRFR2) lacking the 11 N-terminal amino acids of native sauvagine, wherein the N-terminal amino acid of said antagonist is a charged amino acid. Furthermore, the present invention relates to a polynucleotide encoding the antagonist of the present invention, a vector comprising the polynucleotide of the present invention, and a host comprising the polynucleotide or vector of the present invention. Also described are a method for producing the antagonist of the present invention, antibodies directed against the antagonist of the present invention, as well as anti-idiotypic antibodies directed against the antibody of the present invention. The present invention also relates to pharmaceutical and diagnostic compositions comprising the antagonist, the polynucleotide, the vector, the antibody, and/or the anti-idiotypic antibody of the present invention. Furthermore, the present invention relates to a kit comprising one or more of the above mentioned compounds of the present invention and to the use of one or more of these compounds for the preparation of a pharmaceutical composition for preventing and/or treating a Corticotropin-Releasing Factor Receptor, type 2 (CRFR2)-associated disease.

Corticotropin-releasing factor (CRF), believed to synchronize the endocrine, autonomic, immunologic and behavioral responses to stress, was characterized as a 41-residue polypeptide (Spiess, J., J. Rivier, C. Rivier, and W. Vale, *Proc. Natl. Acad. Sci. USA* 78: 6517–6521, 1981) on the basis of its ability to stimulate the secretion of adrenocorticotropic hormone (ACTH) from the anterior pituitary (Vale, W., J. Spiess, C. Rivier, and J. Rivier, *Science* 213: 1394–1397, 1981).

CRF exhibits its activity through G protein-coupled receptors. CRF receptor, type 1 (CRFR1), mainly found in pituitary and brain was cloned from human, mouse, rat, chicken, and frog (Vita, N., P. Laurent, S. Lefort, P. Chalon, J.-M. Lelias, M. Kaghad, G. Le Fur, D. Caput, and P. Ferrara, *FEBS Lett.* 335: 1–5, 1993; Chen, R., K. A. Lewis, M. H. Perrin, and W. Vale, *Proc. Natl. Acad. Sci. USA* 90: 8967–8971, 1993; Perrin, M. H., C. J. Donaldson, R. Chen, K. A. Lewis, and W. Vale, Endocrinology 133: 3058–3061, 1993; Chang, C.-P., R. V. Pearse II, S. O'Connell, and M. G. Rosenfeld, *Neuron* 11: 1187–1195, 1993; Yu, J., L. Y. Xie, and A. B. Abou-Samra, *Endocrinology* 137: 192–197, 1996; Dautzenberg, F. M., K. Dietrich, M. R. Palchaudhuri, and J. Spiess, *J. Neurochem.* 69: 1640–1649, 1997). cDNAs coding for two splice variants of CRF receptor, type 2, CRFR2α and CRFR2β, were cloned from brain, heart, and skeletal muscle (Lovenberg, T. W., C. W. Liaw, D. E. Grigoriadis, W. Clevenger, D. T. Chalmers, E. B. De Souza, and T. Oltersdorf, *Proc. Natl. Acad. Sci. USA* 92: 836–840, 1995; Perrin, M., C. Donaldson, R. Chen, A. Blount, T. Berggren, L. Bilezikjian, P. Sawchenko, and W. Vale, *Proc. Natl. Acad. Sci. USA* 92: 2969–2973, 1995; Kishimoto, T., R. V. Pearse II, C. R. Lin, and M. G. Rosenfeld, *Proc. Natl. Acad. Sci. USA* 92: 1108–1112, 1995; Stenzel, P., R. Kesterson, W. Yeung, R. D. Cone, M. B. Rittenberg, and M. P. Stenzel-Poore, *Mol. Endocrinol.* 9: 637–645, 1995). In rodents, CRFR2α has been exclusively found in the central nervous system (CNS), whereas CRFR2β is predominantly distributed in the periphery. In humans, both receptor subtypes have been found in the CNS (Valdenaire, O., T. Giller, V. Breu, J. Gottowik, and G. Kilpatrick, *Biochim. Biophys. Acta* 1352: 129–132, 1997). Recently, it has been proposed that urocortin (Ucn), a natural CRF analog, is the endogenous ligand to CRFR2 (Vaughan, J., C. Donaldson, J. Bittencourt, M. H. Perrin, K. Lewis, S. Sutton, R. Chan, A. V. Turnbull, D. Lovejoy, C. Rivier, J. Rivier, P. E. Sawchenko, and W. Vale, *Nature* (London) 378: 287–292, 1995).

CRF is assumed to play a major role in a number of neuropsychiatric diseases including affective disorders, anxiety disorders, anorexia nervosa and Alzheimer's disease (Behan, D. P., S. C. Heinrichs, J. C. Troncoso, X. J. Liu, C. H. Kawas, N. Ling, and E. B. De Souza, *Nature* (*London*) 378: 284–287, 1995). There is substantial interest in the design and synthesis of CRF antagonists acting selectively at one of the different CRF forms. After the discovery of potent peptide antagonists based on the N-terminally truncated amino acid sequence of human/rat CRF (h/rCRF) (Rivier, J., C. Rivier, R. Galyean, A. Miranda, C. Miller, A. G. Craig, G. Yamamoto, M. Brown, and W. Vale, *J. Med. Chem.* 36: 2851–2859, 1993; Hernandez, J. F., W. Kornreich, C. Rivier, A. Miranda, G. Yamamoto, J. Andrews, Y. Tache, W. Vale, and J. Rivier, *J. Med. Chem.* 36: 2860–2867, 1993; Miranda, A., S. C. Koerber, J. Gulyas, S. L. Lahrichi, A. G. Craig, A. Corrigan, A. Hagler, C. Rivier, and J. Rivier, *J. Med. Chem.* 37: 1450–1459, 1994; Gulyas, J., C. Rivier, M. Perrin, S. C. Koerber, S. Sutton, A. Corrigan, S. L. Lahrichi, A. G. Craig, W. Vale, and J. Rivier, *Proc. Natl. Acad. Sci. USA* 92: 10575–10579, 1995; Miranda, A., S. L. Lahrichi, J. Gulyas, S. C. Koerber, A G. Craig, A. Corrigan, C. Rivier, W. Vale, and J. Rivier, *J. Med. Chem.* 40: 3651–3658, 1997), several CRFR1-selective nonpeptidic antagonists have been developed (Chen, C., R. Dagnino, Jr., E. B. De Souza, D. E. Grigoriadis, C. Q. Huang, Kjung-II Kim, Z. Liu, T. Moran, T. R. Webb, J. P. Whitten, Y. F. Xie, and J. R. McCarthy, *J. Med. Chem.* 39: 4358–4360, 1996; Schulz, D. W., R. S. Mansbach, J. Sprouse, J. P. Braselton, J. Collins, M. Corman, A. Dunaiskis, S. Faraci, A. W. Schmidt, T. Seeger, P. Seymour, F. D. Tingley III, E. N. Winston, Y. L. Chen, and J. Heym, *Proc. Natl. Acad. Sci. USA* 93: 10477–10482, 1996; Christos, T. E., and A. Arvanitis, *Expert Opinion On Therapeutic Patents* 8: 143–152, 1998) which attenuate CRF-mediated seizure (Baram, T. Z., D. T. Chalmers, C. Chen, Y. Koutsoukos, and E. B. De Souza, *Brain Research* 770: 89–95, 1997) or interleukin-1β-induced fever or exhibit anxiolytic activity in vivo (Lundkvist, J., Z. Chai, R. Teheranian, H. Hasanvan, T. Bartfai, F. Jenck, U. Widmer, and J.-L. Moreau, *Eur. J. Pharmacol.* 309: 195–200, 1996). However, the fact that CRF antagonist α-helical $CRF_{(9-41)}$ exhibits different inhibitory potencies in three different in vivo bioassay systems (Fisher, L., C. Rivier, J. Rivier, and M. Brown, *Endocrinology* 129: 1312–1316, 1991) suggests that distinct physiological functions of endogenous CRF or Ucn are mediated via CRFR1, CRFR2 or both receptor types.

Thus, the technical problem underlying the present invention was to develop CRFR2-specific antagonists to permit discrimination between receptor type-specific functions, e.g., in the brain and peripheral organs.

The solution to said technical problem is provided by the embodiments characterized in the claims.

Accordingly, the present invention relates to an antagonist of the ligand of the Corticotropin-Releasing Factor Receptor, type 2 (CRFR2) lacking the 8 to 10 N-terminal amino acids of native sauvagine.

In accordance with the present invention the term "ligand" encompasses any molecule capable of specifically binding to the Corticotropin-Releasing Factor Receptor, type 2 (CRFR2), including, e.g., (the) naturally occurring, endogenous ligand(s) of CRFR2, or any compound(s) recombinantly or chemically synthesized or biochemically modified and capable of binding and activating CRFR2. The term "CRFR2-specific", "CRFR2-selective", "CRFR2-specificity" or "CRFR2-selectivity" as used in accordance with the present invention denotes a value which is higher than 30, preferably higher than 45, and more preferred higher than 70, and calculated according to the equation mentioned in the legend to table 1. Thus, as used in accordance with the present invention, e.g., a "CRFR2-specific" antagonist is not meant to exclusively bind to CRFR2, but to bind to CRFR2 with an at least 30-fold, preferably 45-fold, and more preferred 70-fold higher selectivity than astressin, which exhibits a similar affinity for CRFR1 and CRFR2, in particular CRFR2β.

Studies which have been carried out in accordance with the present invention surprisingly revealed that deletion of the 8 to 10 N-terminal amino acids of native sauvagine, which is a potent non-selective activator of CRFR, renders this compound a highly specific antagonist for CRFR2.

In a preferred embodiment the antagonist of the present invention lacks the 10 N-terminal amino acids of native sauvagine.

In a more preferred embodiment the antagonist of the present invention comprises the amino acid sequence $Xaa_1$-$Xaa_2$-Leu—Leu-Arg-Lys-Met-Ile-Glu-Ile-Glu-Lys-Gln-Glu-Lys-Glu-Lys-Gln—Gln-Ala-Ala-Asn-Asn-Arg-Leu—Leu—Leu-Asp-Thr-Ile-$NH_2$ (SEQ ID NO: 1), wherein $Xaa_1$ is a neutral amino acid, and $Xaa_2$ is a changed amino acid.

In another more preferred embodiment of the antagonist of the present invention, $Xaa_1$ is a hydrophobic amino acid, and $Xaa_2$ is Glu or His.

In an even more preferred embodiment of the antagonist of the present invention $Xaa_1$ is Leu.

In a further more preferred embodiment, $Xaa_1$ is a polar amino acid and $Xaa_2$ is Glu or His.

In a still more preferred embodiment of the antagonist of the present invention $Xaa_1$ is Tyr.

It is envisaged that antagonists of the present invention comprising Tyr as the N-terminal amino acid can be advantageously used to be radioactively labelled with, e.g., $^{125}I$. Such compounds may then be employed in in vivo or in vitro experiments for the detection of CRFR2 binding sites. Although antagonists $^{125}I$-labelled via His are also encompassed by the present invention, antagonists labelled via Tyr are preferred because the labelling reaction is easier to perform from the technical point of view, and the labelled compound is more stable and, therefore, easier to handle.

In a further even more preferred embodiment of the antagonist of the present invention $Xaa_1$ is in the D-configuration.

In a further still more preferred embodiment of the antagonist of the present invention $Xaa_1$ is D-Leu or D-Tyr.

In a most preferred embodiment of the antagonist of the present invention $Xaa_2$ is Glu.

In another still more preferred embodiment of the antagonist of the present invention $Xaa_1$ is D-Phe.

In another most preferred embodiment of the antagonist of the present invention $Xaa_2$ is His.

In another embodiment, the present invention relates to an antagonist of the ligand of the Corticotropin-Releasing Factor Receptor, type 2 (CRFR2) lacking the 11 N-terminal amino acids of native sauvagine, wherein the N-terminal amino acid of said antagonist is a charged amino acid.

In a preferred embodiment, said charged amino acid is positively charged.

In a more preferred embodiment, said charged amino acid is His.

In another preferred embodiment, the antagonist of the present invention comprises a phenyldiazirine group coupled to the N-terminal amino acid of said antagonist. Antagonists of the present invention comprising a phenyldiazirine group are envisaged to be used, e.g., in photoaffinity labelling experiments. Accordingly, these compounds can be advantageously used to characterize antagonistic binding sites of CRFR2β receptor systems.

In a more preferred embodiment, said phenyldiazirine group is a 4-(1-azi-2,2,2-trifluoroethyl)benzoyl (ATB)-group.

In a further embodiment the present invention relates to a polynucleotide encoding the antagonist of the present invention.

The polynucleotide of the present invention may be, e.g., DNA, cDNA, RNA or synthetically produced DNA or RNA or a recombinantly produced chimeric nucleic acid molecule comprising any of those polynucleotides either alone or in combination.

In another embodiment the present invention relates to a vector comprising the polynucleotide of the present invention.

The vector of the present invention may be, e.g., a plasmid, cosmid, virus, bacteriophage or another vector used conventionally in genetic engineering, and may comprise further genes such as marker genes which allow for the selection of said vector in a suitable host cell and under suitable conditions.

In a preferred embodiment of the vector of the present invention the polynucleotide is operatively linked to an expression control sequence. Said expression control sequence allows expression in prokaryotic or eukaryotic cells. Expression of said polynucleotide comprises transcription of the polynucleotide into a translatable mRNA. Regulatory elements ensuring expression in eukaryotic cells, preferably mammalian cells, are well known to those skilled in the art. They usually comprise regulatory sequences ensuring initiation of transcription and optionally poly-A signals ensuring termination of transcription and stabilization of the transcript. Additional regulatory elements may include transcriptional as well as translational enhancers, and/or naturally-associated or heterologous promoter regions.

Possible regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Beside elements which are responsible for the initiation of transcription such regulatory elements may also comprise transcription termination signals, such as the SV40-poly-A site or the tk-poly-A site, downstream of the polynucleotide. Furthermore, depending on the expression system used leader sequences capable of directing the polypeptide to a cellular compartment or secreting it into the medium may be added to the coding sequence of the polynucleotide of the invention and are well known in the art. The leader sequence(s) is (are) assembled in appropriate phase with translation, initiation and termination sequences, and preferably, a leader sequence capable of directing secretion of translated protein, or a portion thereof, into the periplasmic space or extracellular medium. Optionally, the heterologous sequence can encode a fusion protein including an C- or N-terminal identification peptide imparting desired characteristics, e.g., stabilization or simplified purification of expressed recombinant product. In this context, suitable expression vectors are known in the art such as Okayama-Berg cDNA expression vector pcDV1 (Pharmacia), pCOM8, pRc/CMV, pcDNA1, pcDNA3 (In-vitrogene), or pSPORT1 (GIBCO BRL).

Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences.

Furthermore, the present invention relates to a host comprising the polynucleotide or vector of the present invention.

Said host may be a prokaryotic or eukaryotic cell. The polynucleotide or vector of the invention which is present in the host cell may either be integrated into the genome of the host cell or it may be maintained extrachromosomally.

The host cell can be any prokaryotic or eukaryotic cell, such as a bacterial, insect, fungal, plant, animal or human cell. Preferred fungal cells are, for example, those of the genus *Saccharomyces*, in particular those of the species *S. cerevisiae*. The term "prokaryotic" is meant to include all bacteria which can be transformed or transfected with a polynucleotide or vector of the present invention for the expression of the antagonist of the present invention. Prokaryotic hosts may include gram negative as well as gram positive bacteria such as, for example, *E. coli, S, typhimurium, Serratia marcescens* and *Bacillus subtilis*. The term "eukaryotic" is meant to include yeast, higher plant, insect and preferably mammalian cells. Depending upon the host employed in a recombinant production procedure, the antagonist encoded by the polynucleotide of the present invention may or may not be post-translationally modified. A polynucleotide of the invention can be used to transform or transfect the host using any of the techniques commonly known to those of ordinary skill in the art. Furthermore, methods for preparing fused, operably linked genes and expressing them in, e.g., mammalian cells and bacteria are well-known in the art (e.g. Sambrook et al., Molecular Cloning: A Laboratory Manual, Cold Spring Harbor Laboratory, Cold Spring Harbor, N.Y., 1989). The genetic constructs and methods described therein can be utilized for expression of the antagonist of the present invention in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic animals, preferably mammals, comprising host cells of the invention may be used for the large scale production of the antagonist of the present invention.

The present invention also relates to a method for producing the antagonist of the present invention, said method comprising culturing the host of the present invention under conditions that cause the synthesis of said antagonist, and recovering said antagonist from the culture.

Depending on the specific construct and condition used, the antagonist may be recovered from the host cells, from the culture medium or from both.

The present invention further relates to an antagonist obtainable by the method of the present invention.

Alternatively, the antagonist of the present invention can be chemically synthesized according to methods well known in the art, e.g., solid phase synthesis with Fmoc or t-boc chemistry (see also, e.g., Rühmann, A., A. K. E. Köpke, F. M. Dautzenberg, and J. Spiess, *Proc. Natl. Acad. Sci. USA* 93: 10609–10613, 1996).

In another embodiment the present invention relates to an antibody directed against the antagonist of the present invention.

In a further embodiment the present invention relates to an anti-idiotypic antibody directed against the antibody of the present invention.

The antibodies of the present invention may be monoclonal antibodies, polyclonal antibodies, single chain antibodies, humanized antibodies, or fragments thereof that specifically bind the antagonist of the present invention or the antibody directed against the antagonist of the present invention. Bispecific antibodies, synthetic antibodies, antibody fragments, such as Fab, Fv or scFv fragments etc., or chemically modified derivatives of any of these are also encompassed by the present invention. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof can be obtained by using methods which are described, e.g., in Harlow and Lane "Antibodies, A Laboratory Manual", CSH Press, Cold Spring Harbor, 1988. The production of chimeric antibodies is described, for example, in WO89/09622. Methods for the production of humanized antibodies are described in, e.g., EP-A1 0 239 400 and WO90/07861. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. As discussed above, the antibodies of the invention may exist in a variety of forms besides complete antibodies; including, for example, Fv, Fab and F(ab)2, as well as in single chains; see e.g. WO88/09344.

The present invention also relates to a pharmaceutical composition comprising the antagonist, the polynucleotide, the vector, the antibody and/or the anti-idiotypic antibody of the present invention and optionally a pharmaceutically acceptable carrier and/or diluent.

Examples of suitable pharmaceutical carriers are well known in the art and include phosphate buffered saline solutions, water, emulsions, such as oil/water emulsions, various types of wetting agents, sterile solutions etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical or intradermal administration. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. The compositions of the invention may be administered locally or systemically. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Furthermore, the pharmaceutical composition of the invention may comprise further agents depending on the intended use of the pharmaceutical composition.

Furthermore, the present invention relates to a diagnostic composition comprising the antagonist, the polynucleotide, the vector, the antibody and/or the anti-idiotypic antibody of the present invention.

The present invention further relates to a kit comprising the antagonist, the polynucleotide, the vector, the antibody and/or the anti-Idiotypic antibody of the present invention.

The components of the diagnostic composition and/or the kit of the invention may be packaged in containers such as vials, optionally in buffers and/or solutions. If appropriate, one or more of said components may be packaged in one and the same container. Additionally or alternatively, one or more of said components may be adsorbed to solid support such as, e.g., a nitrocellulose filter or nylon membrane, or to the well of a microtiter plate.

In another embodiment the present invention relates to the use of the antagonist, the polynucleotide, the vector, the antibody and/or the anti-idiotypic antibody of the present invention for the preparation of a pharmaceutical composition for preventing and/or treating a Corticotropin-Releasing Factor Receptor, type 2 (CRFR2) associated disease.

In a preferred embodiment of the antagonist or the use of the present invention said CRFR2 is CRFR2α or CRFR2β.

In another preferred embodiment the use of the present invention is for preventing and/or treating affective disorders, gastric intestinal diseases, cardiopathic diseases, psychiatric diseases, preferably eating disorders, anxiety disorders or anorexia nervosa, and/or Alzheimer's disease.

The present invention also relates to the use of the antagonist, the polynucleotide, the vector, the antibody and/or the anti-idiotypic antibody of the present invention for the investigation of CRF receptor type-specific functions.

The documents cited herein are herewith incorporated by reference.

Abbreviations used throughout the description, the figure legends, and the examples are as follows: IUPAC rules are used for the nomenclature of peptides including one letter codes for amino acids. AAA: amino acid analysis; ACTH: adrenocorticotropic hormone; ANOVA: one-way analysis of variance; astressin: {cyclo(30-33)[DPhe$^{12}$, Nle$^{21,38}$, Glu$^{30}$, Lys$^{33}$]h/rCRF$_{(12-41)}$}; BSA: bovine serum albumin; cAMP: adenosine 3', 5'-cyclic monophosphate; CRF: corticotropin-releasing factor (h=human, o=ovine, r=rat); CRFR: CRF receptor; DIEA: N,N-diisopropylethylamine; DMF: dimethylformamide; Fmoc: 9-fluorenylmethoxycarbonyl; HBTU: O-(benzotriazol-1-yl)-N,N,N',N'-tetramethyluronium hexafluorophophate; HEK: human embryonic kidney; HOAc: acetic acid; HOBt: 1-hydroxybenzotriazole; $^{125}$I: $^{125}$I-iodinated; MeCN: acetonitrile; MS: mass spectrometry; NMP: N-methylpyrrolidone-2; OAll: O-allyl; OAlloc: O-allyloxycarbonyl; Pd$^0$[PPh$_3$]$_4$: tetrakis-(triphenylphosphine)-palladium; RP-HPLC: reverse phase high-performance liquid chromatography; SAR: structure-activity relationship; Svg: sauvagine; TFA: trifluoroacetic acid; Ucn: urocortin.

The figures show:

FIG. 1:
Comparison of the amino acid sequence of human/rat corticotropin-releasing factor (h/rCRF)(SEQ ID NO: 2) with ovine corticotropin-releasing factor (oCRF) (SEQ ID NO: 3), rat urocortin (rUcn) (SEQ ID NO: 4), sauvagine (Svg) (SEQ ID NO: 5), and astressin (SEQ ID NO: 6). Identical amino acids are shaded.

Figure 2:
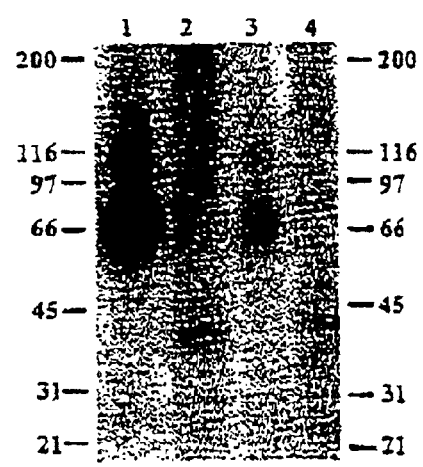

FIG. 2:
Chemical cross-linking of [$^{125}$I-Tyr$^0$]oCRF or [$^{125}$I-Tyr$^0$]Svg to membrane homogenates of human embryonic kidney (HEK) 293 cells stably transfected with cDNA coding for rat CRF receptor, type 1 (rCRFR1) (lanes 1 and 2) or mouse CRF receptor, type 2β (mCRFR2β) (lanes 3 and 4), respectively. Fifty µg of total membrane protein was labeled with approximately 100,000 cpm of [$^{125}$I-Tyr$^0$]oCRF (lanes 1 and 2) and [$^{125}$I-Tyr$^0$]Svg (lanes 3 and 4), and incubated (37° C., 30 min) in the presence (lane 2 and 4) or absence (lane 1 and 3) of 2000 units PNGase.

Figure 3:
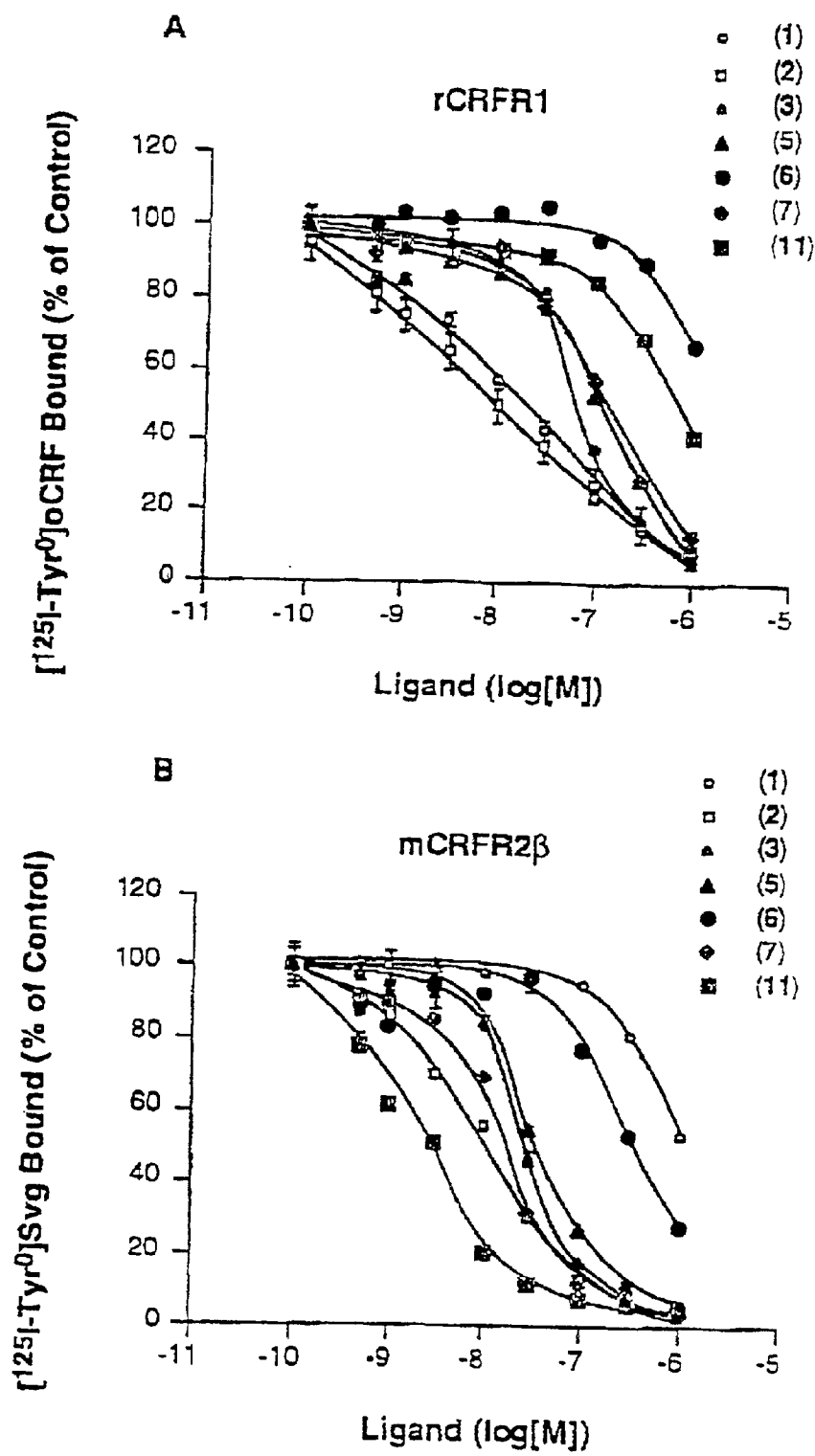

FIG. 3:
Displacement of [$^{125}$I-Tyr$^0$]oCRF (A) or [$^{125}$I-Tyr$^0$]Svg (B) bound to membrane homogenates of HEK 293 cells stably transfected with cDNA coding for rat CRF receptor, type 1 (rCRFR1) (A), or mouse CRF receptor, type 2β (mCRFR20) (B), by oCRF (compound 1, ○), Svg (compound 2, □), astressin (compound 3, △), [DPhe$^{12}$, Nle$^{21,38}$]h/rCRF$_{(12-41)}$ (compound 5, ▲), [DPhe$^{12}$]oCRF$_{(12-41)}$ (compound 6, ●), [DPhe$^{11}$]rUcn$_{(11-40)}$ (compound 7, ◆), and [DPhe$^{11}$, His$^{12}$]Svg$_{(11-40)}$ (compound 11, ■). The error bars represent the SEM and are not shown when smaller than the symbol size.

Figure 4:
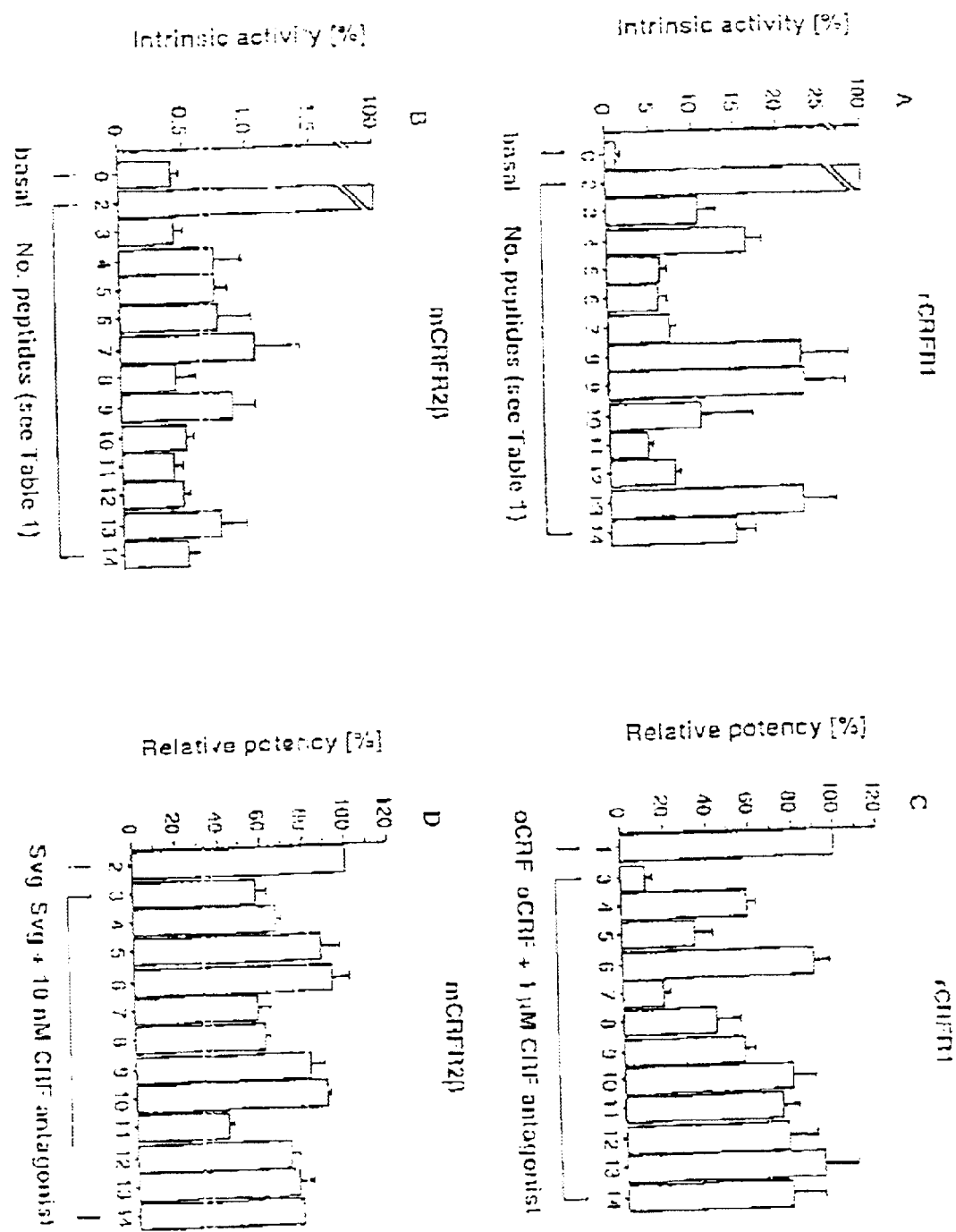

FIG. 4:
Potency of 1 µM CRF antagonist (compounds 3–14) to stimulate cAMP production in transfected HEK 293 cells (% IA, intrinsic activity) (A, B). Efficacy of CRF antagonists (c=1 µM for rCRFR1, and c=10 nM for mCRFR2β) to inhibit cAMP production in transfected HEK 293 cells stimulated by 1 nM oCRF (compound 1 for rCRFR1) and 1 nM Svg (compound 2 for mCRFR2β) (relative in vitro potency) (C, D). Data is the mean from 3–11 experiments. The error bars represent the SEM.

The examples illustrate the invention.

EXAMPLE 1

Synthesis and Analysis of Peptides

Different truncated and conformationally constrained analogs of corticotropin-releasing factor (CRF) were synthesized on the basis of the amino acid sequences of human/rat CRF (h/rCRF), ovine CRF (oCRF), rat urocortin (rUcn), or sauvagine (Svg) (0.1 mmol scale) with Fmoc chemistry on TentaGel S RAM resin (Rapp, Tübingen, F.R.G.) with a model ABI 433A peptide synthesizer (Applied Biosystems).

Comparison of the amino acid sequences of oCRF, rUcn and Svg with the sequence of h/rCRF reveals 45–83% amino acid identity. The CRF ligands mentioned share high amino acid identity at the N-terminus (47%) stretching from amino acid 2-20 (h/rCRF and oCRF) and 1-19 (rUcn and Svg), but little at the C-terminus (14%) of the peptides stretching from amino acid 21-41 and 20-40, respectively (FIG. 1). It was assumed that the ligand receptor interactions of the truncated forms of the CRF peptides ranging from amino acid 11-40 (rUcn and Svg) or 12-41 (h/rCRF and oCRF) acted differently than the full-length CRF peptides on CRFR1 or CRFR2 (Dautzenberg, F. M., K. Dietrich, M. R. Palchaudhuri, and J. Spiess, *J. Neurochem.* 69: 1640–1649, 1997; Vaughan, J., C. Donaldson, J. Bittencourt, M. H. Perrin, K. Lewis, S. Sutton, R. Chan, A. V. Turnbull, D. Lovejoy, C. Rivier, J. Rivier, P. E. Sawchenko, and W. Vale, *Nature (London)* 378: 287–292, 1995; Donaldson, C. J., S. W. Sutton, M. H. Perrin, A. Z. Corrigan, K. A. Lewis, J. E. Rivier, J. M. Vaughan, and W. W Vale, *Endocrinology* 137: 2167–2170, 1996; Gottowik, J., V. Goetschy, S. Henriot, E. Kitas, B. Fluhman, R. G. Clerc, J. L. Moreau, F. J. Monsma, and G. J. Kilpatrick, *Neuropharmacol.* 36: 1439–1446, 1997).

For the synthesis of the cyclized CRF analogs, astressin and cyclo(29-32)[DPhe$^{11}$, Glu$^{29}$, Lys$^{32}$]rUcn$_{(11-40)}$, the amino acid derivatives Fmoc-L-Glu(OAll)-OH and Fmoc-L-Lys(Alloc)-OH (PerSeptive Biosystems GmbH, Hamburg, F.R.G.) were used. The side-chain-protected peptides were reacted with Pd$^0$[PPh$_3$]$_4$ in HOAc/N-methylaniline/dichloromethane (v/v; 2:1:40) for three hours and then cyclized with HOBt/HBTU in DMF and DIEA in NMP for eight hours. After removal of the N-terminal Fmoc group with piperidine in NMP, the peptides were cleaved from the resin under standard conditions. The crude peptides were purified by preparative reverse phase high-performance liquid chromatography (RP-HPLC) performed on a Waters Prep Nova-Pak HR C$_{18}$ silica gel column (5×30 cm, 6-μm particle size, 6-nm pore size) with a mixture of aqueous 0.1% trifluoroacetic acid and MeCN (see Table 5). The mass spectra of the purified peptides were measured with a plasma desorption mass spectrometer (Biolon 20, Uppsala). Amino acid analysis (AAA) was performed after hydrolysis of peptides (6 N HCl, 3 hr. 150° C.) with a Beckman High Performance Analyzer System 6300 (Beckman, San Remon).

EXAMPLE 2

Binding of CRF Agonists and Antagonists to rCRFR1

CRF agonists and antagonists were tested in an in vitro assay for their ability to displace [$^{125}$I-Tyr$^0$]oCRF or [$^{125}$I-Tyr$^0$]Svg from membranes of HEK-rCRFR1 cells (Rühmann, A., A. K. E. Köpke, F. M. Dautzenberg, and J. Spiess, *Proc. Natl. Aced. Sci. USA* 93: 10609–10613, 1996) or HEK-mCRFR2β cells (Kishimoto, T., R. V. Pearse II, C. R. Lin, and M. G. Rosenfeld, *Proc. Natl. Acad. Sci. USA* 92: 1108–1112, 1995). Binding assays were performed in 96-well MultiScreen plates (Millipore, Eschborn, Germany) with GF/B filters (pore size 1.0 μm). Fifty-microliters of membrane suspension (25 μg of protein from HEK-rCRFR1 cells; 50 μg of protein from HEK-mCRFR2β cells) was added to a plate containing CRF peptides (c=0–1 μM) and 50,000 cpm of either [$^{125}$I-Tyr$^0$]oCRF (specific activity 81.4 TBq/mmol, 68.25 μM, DuPont NEN, Boston) for the analysis of rCRFR1 or [$^{125}$I-Tyr$^0$]Svg (specific activity 81.4 TBq/mmol, 68.25 μM, DuPont NEN, Boston) for the analysis of mCRFR2β in 100 μl incubation buffer (50 mM Tris/Cl, 5 mM MgCl$_2$, 2 mM EGTA, 100,000 kallikrein inhibitor units per liter of Trasylol (Bayer, Leverkusen), 1 mM dithiothreitol, 1 mg/ml BSA, pH 7.4). After incubation (60 min, 23° C.), membrane suspension was aspirated through the plate, followed by two washes with assay buffer (0.2 ml, 23°). Radioactivity of the punched filters was measured with a 1470 WIZARD automatic gamma counter (Berthold, Hannover). Specific binding of [$^{125}$I-Tyr$^0$]oCRF or [$^{125}$I-Tyr$^0$]Svg to membranes of transfected cells was calculated by substration of unspecific binding found in the presence of 1 μM of nonlabeled ligand from total binding. Data analysis was achieved with the nonlinear curve fitting program LIGAND. Statistical analysis was performed with ANOVA, and significant differences between groups were determined by post hoc comparison using the Dunn test.

EXAMPLE 3

Chemical Cross-Linking with [$^{125}$I-Tyr$^0$]oCRF or [$^{125}$I-Tyr$^0$]Svg

Chemical cross-linking was carried out in 1.5 ml polypropylene tubes (Sigma, Deisenhofen, Germany) as for the binding assay except that no BSA was used. Samples (50 μg and 100 μg of protein from membrane fractions of HEK-rCRFR1 cells and HEK-mCRFR2β cells, respectively) were reacted with 10 μl of disuccinimidyl substrate (1.5 mM in dimethylsulfoxide, 23° C., 20 min) after incubation with ligand (V=300 μl, 100,000 cpm, 1 hr, 23° C.). The reaction was terminated by the addition of 1.0 ml of ice-cold buffer (10 mM Tris/Cl, 1 ml EDTA, pH 7.0, 4° C.). In some experiments, the chemically cross-linked receptor was deglycosylated with PNGase (New England Biolabs, Schwalbach). Samples were then heated (100° C., 5 min) and subjected to SDS PAGE. Autoradiography was carried out on a BAS-IP NP 2040P imaging plate. Radioactivity was monitored with a Fujix BAS 2000 scanner (Raytest, Straubenhardt). Gel documentation was accomplished with the program TINA (Raytest).

EXAMPLE 4

Determination of cAMP Stimulation

HEK-rCRFR1 cells or HEK-mCRFR2β cells were incubated with different CRF agonists in the presence or absence of 1 μM or 10 nM antagonist, or CRF antagonist (c=1 μM) alone. After removal of the medium, cells were lyzed with aqueous 6% trichloroacetic acid (5 min, 100° C.) (Rühmann, A., A. K. E. Köpke, F. M. Dautzenberg, and J. Spiess, *Proc. Natl. Acad. Sci. USA* 93: 10609–10613, 1996). The cell lysates were stored at −70° C. until assayed with a RIA kit (Amersham, Little Chalfont). Data analysis was achieved with the sigmoidal dose-response curve fitting program ALLFIT. Statistical significance was determined across groups with ANOVA, and significant differences between groups were determined by post hoc comparison using the Dunn test.

EXAMPLE 5

Displacement of [$^{125}$I-Tyr$^0$]oCRF or [$^{125}$I-Tyr$^0$]Svg from Recombinant rCRFR1 or mCRFR2β by CRF Analogs Membrane homogenates of human embryonic kidney (HEK) 293 cells stably transfected with cDNA coding for rat CRF receptor, type 1 (rCRFR1) or mouse CRF receptor, type 2β (mCRFR2β) were prepared according to standard protocols (see, e.g., Sambrook et al., Molecular Cloning: A Laboratory Manual, 2nd. Edition, Cold Spring Habor Laboratory Press, Cold Spring Harbor, N.Y., 1989; Ausubel et al., Current Protocols in Molecular Biology, Green Publishing Associates and Wiley Interscience, NY, 1989). The specific binding of [$^{125}$I-Tyr$^0$]oCRF to membranes of HEK-rCRFR1 cells was found to be 93% when the radioligand was displaced by oCRF. In analogous displacement experiments with Svg, the specific binding of [$^{125}$I-Tyr$^0$]Svg to membranes of HEK-mCRFR2β cells was determined to be 94%. No specific binding of the two radioactively labeled CRF analogs to membranes of nontransfected HEK 293 cells could be observed. These data could be confirmed when [$^{125}$I-Tyr$^0$]oCRF and [$^{125}$I-Tyr$^0$]Svg were chemically cross-linked to rCRFR1 and mCRFR2β, respectively. The molecular weight of both cross-linked receptors was 66,000. After deglycosylation with PNGase, molecular weights of 43,000 and 41,000 were found for crosslinked mCRF2β and rCRFR1, respectively (FIG. 2), which are in agreement with the molecular weight predicted on the basis of DNA data (Perrin, M. H., C. J. Donaldson, R. Chen, K. A. Lewis, and W. Vale, Endocrinology 133: 3058–3061, 1993; Kishimoto, T., R. V. Pearse II, C. R. Lin, and M. G. Rosenfeld, Proc. Natl. Acad. Sci. USA 92: 1108–1112, 1995). The difference of 2,000 between the molecular weights of rCRFR1 and mCRFR2β is probably due to the longer amino acid sequence of mCRFR2β. No chemical cross-links could be observed with either radioligand to nontransfected HEK 293 cells.

As expected for the CRF peptide agonists (Dautzenberg, F. M., K. Dietrich, M. R. Palchaudhuri, and J. Spiess, J. Neurochem. 69: 1640–1649, 1997; Donaldson, C. J., S. W. Sutton, M. H. Perrin, A. Z. Corrigan, K. A. Lewis, J. E. Rivier, J. M. Vaughan, and W. W Vale, Endocrinology 137: 2167–2170, 1996; Gottowik, J., V. Goetschy, S. Henriot, E. Kitas, B. Fluhman, R. G. Clerc, J. L. Moreau, F. J. Monsma, and G. J. Kilpatrick, Neuropharmacol. 36: 1439–1446, 1997), oCRF and Svg exhibited similar high-affinity binding to rCRFR1 (oCRF: $K_d$=0.6±0.1 nM, Svg: $K_d$=0.7±0.1 nM), but differed significantly in their binding to mCRFR2β (oCRF: $K_d$=162.4±37.6 nM, Svg: $K_d$=4.5±0.6 nM) (Table 1, FIG. 3).

For the binding of the CRF antagonists, (α-helical CRF$_{(9-41)}$ and [DPhe$^{12}$, Nle$^{21,38}$]h/rCRF$_{(12-41)}$ described earlier (Gulyas, J., C. Rivier, M. Perrin, S.C. Koerber, S. Sutton, A. Corrigan, S. L. Lahrichi, A. G. Craig, W. Vale, and J. Rivier, Proc. Natl. Acad. Sci. USA 92: 10575–10579, 1995) to rCRFR1, $K_d$ values of 60.3±10.6 nM and 46.4±9.4 nM were obtained, respectively. The antagonist astressin (Gulyas, J., C. Rivier, M. Perrin, S.C. Koerber, S. Sutton, A. Corrigan, S. L. Lahrichi, A. G. Craig, W. Vale, and J. Rivier, Proc. Natl. Acad. Sci. USA 92: 10575–10579, 1995), cyclo (30-33)[DPhe$^{12}$, Nle$^{21,38}$, Glu$^{30}$, Lys$^{33}$]h/rCRF$_{(12-41)}$, was found to bind nonselectively with similar affinity to rCRFR1 ($K_d$=5.7±1.6 nM) and mCRFR2β (d=4.0±2.3 nM), whereas α-helical CRF$_{(9-41)}$ and [DPhe$^{12}$, Nle$^{21,38}$]h/rCRF$_{(12-41)}$ showed moderate selectivity for binding to mCRFR2β with $K_d$ values of 6.4±0.9 nM and 17.7±2.2 nM, respectively (Table 1). [DPhe$^{12}$]oCRF$_{(12-41)}$ based on the amino acid sequence of oCRF showed low-affinity binding to rCRFR1 and mCRFR2β with $K_d$ values of 290.2±74.7 nM and 153.8±26.8 nM, respectively (Table 1, FIG. 3). The truncated Ucn analogs [DPhe$^{11}$]rUcn$_{(11-40)}$, [DPhe$^{11}$, Glu$^{12}$]rUcn$_{11-40)}$, [DLeu$^{11}$, Glu$^{12}$]rUcn$_{(11-40)}$, and cyclo(29-32) [DPhe$^{11}$, Glu$^{29}$, Lys$^{32}$]rUcn$_{(11-40)}$ exhibited moderate binding affinity to rCRFR1 with $K_d$ values of 33.0±5.9 nM, 68.2±20.5 nM, 91.1±21.2 nM, and 47.1±8.9 nM, respectively, and revealed little preference for binding to mCRFR2β with $K_d$ values of 5.2±1.5 nM, 9.5±2.0 nM, 27.9±3.4 nM, and 22.4±4.6 nM, respectively (Table 1, FIG. 3).

The Svg-derived peptides [DLeu$^{11}$]Svg$_{(11-40)}$, Svg$_{(11-40)}$, [DPhe$^{11}$]Svg$_{(11-40)}$, and [DPhe$^{11}$, His$^{12}$]Svg$_{(11-40)}$ showed low-affinity binding to rCRFR1 with $K_d$ values of 1670.0±500.0 nM, 831.2±668.8 nM, 237.3±27.7 nM, and 153.6±33.5 nM, respectively, but high affinity binding to mCRFR2, with $K_d$ values of 20.9±4.1 nM, 15.4±2.5 nM, 3.5+0.2 nM, and 1.4±0.4 nM, respectively (Table 1). Thus, [DPhe$^{11}$, His$^{12}$]Svg$_{(11-40)}$, [DLeu$^{11}$]Svg$_{(11-40)}$, [DPhe$^{11}$]Svg$_{(11-40)}$, and Svg$_{(11-40)}$ bound with a 77-, 56-, 47-, and 38-fold higher selectivity to mCRFR2β than astressin, respectively.

ANOVA indicated statistically significant differences in high-affinity binding, F(13,41)=13.17 p=0.0001, of the CRF peptides (compounds 1–14) to cell membranes of HEK-rCRFR1 cells (Table 1). Post hoc comparison demonstrated a significantly lower binding affinity of [DLeu$^{11}$]Svg$_{(11-40)}$ (compound 13) and Svg$_{(11-40)}$ (compound 14) to cell membranes when compared to compounds 1–5, and 7–11 (p=0.0001) (Table 1). Statistically significant differences in high-affinity binding, F(13,36)=20.34 p=0.0001, of oCRF (compound 1) and [DPhe$^{12}$]oCRF$_{(12-41)}$ (compound 6) to cell membranes of HEK-mCRFR2β cells were observed. Post hoc comparison demonstrated a significantly lower binding affinity of oCRF (compound 1) and [DPhe$^{12}$]oCRF$_{(12-41)}$ (compound 6) to cell membranes when compared to compounds 2–5 and compounds 7–14 (p=0.0001) (Table 1).

Thus, in comparison to astressin, the most potent CRF antagonist described to date (Gulyas, J., C. Rivier, M. Perrin, S.C. Koerber, S. Sutton, A. Corrigan, S. L. Lahrichl, A. G. Craig, W. Vale, and J. Rivier, Proc. Natl. Acad. Sci. USA 92: 10575–10579, 1995), the intrinsic activity of [DPhe$^{11}$, His$^{12}$]Svg$_{(11-40)}$ was not significantly different in experiments with HEK-rCRFR1 or HEK-mCRFR2β cells. However, the inhibitory potency of [DPhe$^{11}$, His$^{12}$]Svg$_{(11-40)}$ towards rCRFR1 was found to be 15% of the potency of astressin. This difference was determined to be significant. In contrast, no significant difference between the inhibitory potencies of astressin and [DPhe$^{11}$, His$^{12}$]Svg$_{(11-40)}$ was observed, when HEK-mCRF2β cells were tested (Table 2). The difference between astressin and [DPhe$^{11}$, His$^{12}$]Svg$_{11-40)}$ was even more pronounced in binding experiments (Table 1) which demonstrated that [DPhe$^{11}$, His$^{12}$]Svg$_{(11-40)}$ exhibited in contrast to astressin selective binding to mCRFR2β. On the basis of ligand comparisons, [DPhe$^{11}$, His$^{12}$]Svg$_{(11-40)}$ was thus demonstrated to be a selective, mCRFR2β-directed CRF antagonist with low intrinsic activities directed towards rCRFR1 and mCRFR2α.

In contrast to CRFR2, mammalian CRFR1 has been reported to be nonselective for CRF and CRF-like peptides including the structurally related 40-amino acid peptides Svg and Ucn (Vita, N., P. Laurent, S. Lefort, P. Chalon, J.-M. Lelias, M. Kaghad, G. Le Fur, D. Caput, and P. Ferrara, FEBS Left. 335: 1–5, 1993; Dautzenberg, F. M., K. Dietrich, M. R. Palchaudhuri, and J. Spiess, J. Neurochem. 69: 1640–1649, 1997; Vaughan, J., C. Donaldson, J. Bittencourt, M. H. Perrin, K. Lewis, S. Sutton, R. Chan, A. V. Tumbull, D. Lovejoy, C. Rivier, J. Rivier, P. E. Sawchenko, and W. Vale, Nature (London) 378: 287–292, 1995; Fisher, L., C. Rivier, J. Rivier, and M. Brown, Endocrinology 129: 1312–1316, 1991; Donaldson, C. J., S. W. Sutton, M. H. Perrin, A. Z. Corrigan, K. A. Lewis, J. E. Rivier, J. M. Vaughan, and W. W Vale, Endocrinology 137: 2167–2170, 1996). Experimental data available thus far do not show significant pharmacological differences between mammalian CRFR2α and CRFR2β (Fisher, L., C. Rivier, J. Rivier, and M. Brown, *Endocrinology* 129: 1312–1316, 1991; Donaldson, C. J., S. W. Sutton, M. H. Perrin, A. Z. Corrigan, K. A. Lewis, J. E. Rivier, J. M. Vaughan, and W. W Vale, *Endocrinology* 137: 2167–2170, 1996). On this basis, it is expected that [DPhe$^{11}$, His$^{12}$]Svg$_{(11-40)}$ inhibits CRFR2α similarly as CRFR2β. Indeed, results obtained from in vivo experiments with BALB/c mice showed that [DPhe$^{11}$, His$^{12}$]Svg$_{(11-40)}$ inhibited CRF-mediated behavioral effects in the lateral septum (J. Radulovic, A. Rühmann, T. Liepold and J. Spiess, J. Neurosci. 19 (1999), 5016–5025; D. T. Chalmers, T. W. Lovenberg and E. B. DeSouza, J. Neurosci. 15 (1995), 6340–6350) an area in the brain which exclusively expresses CRF2α-mRNA.

EXAMPLE 6 cAMP Stimulation

The peptide agonists oCRF and Svg exhibited high potency to increase cAMP accumulation in HEK-rCRFR1 cells with EC$_{50}$ values of 0.41±0.08 nM and 0.19±0.05 nM, respectively, but differed significantly in their potencies to stimulate cAMP production in HEK-mCRFR2 β cells with EC$_{50}$ values of 11.79±1.96 nM and 0.23±0.05 nM, respectively.

The CRF antagonists (compounds 3–14, Table 2, FIG. 4) mentioned above were tested for their ability to enhance or inhibit oCRF- and Svg-stimulated cAMP production in transfected HEK 293 cells expressing rCRFR1 (HEK-rCRFR1 cells) and mCRFR2β (HEK-mCRFR2β cells), respectively. Intrinsic activities were measured at peptide concentrations generating maximal formation of cAMP in HEK-rCRFR1 or HEK-mCRFR2β cells. The intrinsic activities of CRF antagonists tested by their effect at a concentration of 1 μM on HEK-rCRFR1 cells ranged from 4–23% of the intrinsic activity of oCRF (compound 1) tested at a concentration of 1 nM. The intrinsic activities of the antagonists tested under equivalent conditions with HEK-mCRFR2β cells were 0.4–0.9% of the intrinsic activity of Svg (compound 2) (Table 2, FIG. 4).

ANOVA indicated statistically significant differences in intrinsic activity, F(12,50)=11.68, p=0.0001, of compounds 3–14 to stimulate CAMP production in HEK-rCRFR1 cells. Post hoc comparison demonstrated a significantly higher intrinsic activity of compounds 8, 9, and 13 when compared to compounds 5, 6, 7, 11, and 12 p=0.001). Compounds 4 and 14 also significantly increased cAMP production in HEK-rCRFR1 cells when compared to the basal level of cAMP in the same cells (p=0.001) (Table 2). ANOVA indicated no statistically significant differences in intrinsic activity of compounds 3–14 to stimulate cAMP production in HEK-mCRFR2β cells. Compound 11 exhibited the lowest intrinsic activity of all tested CRF antagonists in experiments with either recombinant system, HEK-rCRFR1 cells and HEK-mCRFR2β cells (Table 2).

The rank order of potencies for the CRF related peptide antagonists to suppress oCRF-induced cAMP-accumulation in HEK-rCRFR1 cells was as follows: astressin (compound 3) and [DPhe$^{11}$]rUcn$_{(11-40)}$ (compound 7)>[DPhe$^{12}$, Nle$^{21,38}$]h/rCRF$_{(12-41)}$ (compound 5) and [DPhe$^{11}$, Glu$^{12}$]rUcn$_{(11-40)}$ (compound 8)>[DLeu$^{11}$, Glu$^{12}$]rUcn$_{(11-40)}$ (compound 9) and α-helical CRF$_{(9-41)}$ (compound 4)>[DPhe$^{11}$, His$^{12}$]Svg$_{11-40)}$ (compound 11), [DPhe$^{11}$]Svg$_{(11-40)}$ (compound 12), Svg$_{(11-40)}$ (compound 14), and cyclo(29-32)[DPhe$^{11}$, Glu$^{29}$, Lys$^{32}$]rUcn$_{(11-40)}$ (compound 10)>[DPhe$^{12}$]oCRF$_{(12-41)}$ (compound 6) and [DLeu$^{11}$]Svg$_{(11-40)}$ (compound 13). In contrast, the following pharmacological profile was obtained for the inhibition of Svg-stimulated cAMP production in HEK-mCRFR2β cells by CRF antagonists: [DPhe$^{11}$, His$^{12}$]Svg$_{(11-40)}$ (compound 11)>astressin (compound 3), [DPhe$^{11}$]rUcn$_{(11-40)}$ (compound 7), [DPhe$^{11}$, Glu$^{12}$]rUcn$_{(11-40)}$ (compound 8), and α-helical CRF$_{(9-41)}$ (compound 4)>[DPhe$^{11}$]Svg$_{(11-40)}$ (compound 12), [DLeu$^{11}$]Svg$_{(11-40)}$ (compound 13), and Svg$_{(11-40)}$ (compound 14)>[DLeu$^{11}$]rUcn$_{(11-40)}$ (compound 9)>[DPhe$^{12}$, Nle$^{21,38}$]h/rCRF$_{(12-41)}$ (compound 5), cyclo(29-32)[DPhe$^{11}$, Glu$^{29}$, Lys$^{32}$]rUcn$_{(11-40)}$ (compound 10), and [DPhe$^{12}$]oCRF$_{(12-41)}$ (compound 6).

ANOVA indicated statistically significant differences in potency, F(12,39)=7.93, p=0.0001, of compounds 3–14 to inhibit oCRF-stimulated cAMP production in HEK-rCRFR1 cells. Post hoc comparison demonstrated a significantly higher potency of compounds 3 and 7 when compared to compounds 6 (p=0.0001) and compounds 10–14 (p=0.0001). A significantly higher potency was also observed for compound 5 when compared to compounds 6 (p=0.001) and 13 (p=0.0001).

ANOVA indicated statistically significant differences in potency, F(12,65)=6.34, p=0.0001, of compounds 3–14 to inhibit Svg-stimulated cAMP production in HEK-mCRFR2β cells. Post hoc comparison demonstrated a significantly higher potency of compound 11 when compared to compounds 2 and 4 (p=0.001) or compounds 5, 6, 9, 10, and 13 (p=0.0001).

EXAMPLE 7

Synthesis of 4-(1-azi-2.2.2-trifluoroethyl)benzoic Acid 4-(1-azi-2,2,2-trifluoroethyl)benzoic acid was synthesized as described in PCT/EP96/05011.

EXAMPLE 8

Analysis of CRFR2-Selective Antagoinsts Suitable for Radioactive Labelling and Photoaffinity Labelling Experiments Corticotropin-releasing factor (CRF) receptor, type 20 (CRFR20)-selective antagonists based on the truncated amino acid sequence of sauvagine (Svg) were synthesized and characterized. The N-terminal amino acid Leu$^{11}$ in Svg (11-40) was substituted by either tyrosine or a phenyldiazirine, the 4-(1-azi-2,2,2-trifluoroethyl)benzoyl (ATB) group, for radioactive labelling or photoaffinity labelling experiments, respectively. To further increase the binding affinity of the ligands to membrane homogenates of human embryonic kidney (HEK) cells permanently transfected with cDNA coding for rat CRFR1 (rCRFR1) or mouse CRFR2β (mCRFR2β), Glu$^{12}$ was substituted by histidine.

The binding affinity of the compounds to rCRFR1 and mCRFR2β and the potency of the ligands to produce CAMP accumulation (agonistic activity) or inhibit oCRF-(rCRFR1) or Svg-(mCRFR2β) stimulated CAMP production (antagonistic activity) in transfected cells were compared with the binding affinity and potency of antisauvagine-30 {[DPhe$^{11}$, His$^{12}$Svg(11-40)} (compound 11), astressin {cyclo(30-33)[DPhe$^{2}$, Nle$^{21,38}$, Glu$^{30}$, Lys$^{33}$]h/rCRF(12-41) (compound 3) and the photoactivatable astressin analogs ATB-cyclo(30-33)[Nle$^{21,38}$, Glu$^{30}$, Ala$^{32}$, Lys$^{33}$]h/rCRF(13-

41) (compound 15) and ATB-cyclo(30-33)[Nle$^{21,38}$, Glu$^{30}$, Tyr$^{32}$, Lys$^{33}$]h/rCRF(13-41) (compound 16).

Substitution of DPhe$^{11}$ by the phenyldiazirine moiety in ATB-[His$^{12}$]Svg(12-40) (compound 17) did not significantly change the binding affinity, ligand selectivity, and potency of this ligand to CRFR1 and mCRFR2β when compared with antisauvagine-30 (compound 11) (Table 3 and 4). Similar results could be observed for ATB-cyclo(30-33)[(Nle$^{21,38}$, Glu$^{30}$, Ala$^{32}$, Lys$^{33}$]h/rCRF(13-41) (compound 15) when compared with astressin (compound 3)(Table 3 and 4).

Substitution of DPhe$^{11}$ by tyrosine in [Tyr$^{11}$, His$^{12}$]Svg (11-40) (compound 18) or [Tyr$^{11}$]Svg(11-40) (compound 19) decreased the binding affinity of these compounds to rCRFR1 or mCRFR2β by 1.4 to 5.9-fold when compared to antisauvagine-30 (compound 11) or [DPhe$^{11}$]Svg(11-40) (compound 12), respectively, without changing preferable binding to mCRFR2β. Further N-terminal truncation of the amino acid sequence Svg(11-40) by one amino acid and substitution of Glu$^{12}$ by tyrosine completely abolished high-affinity binding of [Tyr$^{12}$]Svg(1240) (compound 20) to mCRFR2β (Table 3).

TABLE 1

Binding constants (K$_d$, [nM]) found for different CRF-related agonists and antagonists when bound to recombinant rCRFR1 with [$^{125}$I-Tyr$^0$]oCRF as competitive ligand or recombinant mCRFR2β with [$^{125}$I-Tyr$^0$]Svg as competitive ligand.

| No. | peptides | [$^{125}$I-Tyr$^0$]oCRF K$_{d(rCRFR1)}$, [nM] | [$^{125}$I-Tyr$^0$]Svg K$_{d(mCRFR2β)}$, [nM] | P | Selectivity$^e$ |
|---|---|---|---|---|---|
| 1 | oCRF | 0.6 ± 0.1 | 162.4 ± 37.6$^c$ | [*] | 0.002 |
| 2 | Svg | 0.7 ± 0.1 | 4.5 ± 0.6 | [**] | 0.109 |
| 3 | astressin | 5.7 ± 1.6 | 4.0 ± 2.3 | N.S. | 1.00 |
| 4 | α-helical CRF$_{(9-41)}$ | 60.3 ± 10.6 | 6.4 ± 0.9 | [**] | 6.61 |
| 5 | [DPhe$^{12}$, Nle$^{21,38}$]h/rCRF$_{(12-41)}$ | 46.4 ± 9.4 | 17.7 ± 2.2 | [*] | 1.84 |
| 6 | [DPhe$^{12}$]oCRF$_{(12-41)}$ | 290.2 ± 74.7 | 153.8 ± 26.8$^d$ | N.S. | 1.32 |
| 7 | [DPhe$^{11}$]rUcn$_{(11-40)}$ | 33.0 ± 5.9 | 5.2 ± 1.5 | [**] | 4.45 |
| 8 | [DPhe$^{11}$, Glu$^{12}$]rUcn$_{(11-40)}$ | 68.2 ± 20.5 | 9.5 ± 2.0 | [*] | 5.04 |
| 9 | [DLeu$^{11}$, Glu$^{12}$]rUcn$_{(11-40)}$ | 91.1 ± 21.2 | 27.9 ± 3.4 | [*] | 2.29 |
| 10 | cyclo(29-32) [DPhe$^{11}$, Glu$^{29}$, Lys$^{32}$]rUcn$_{(11-40)}$ | 47.1 ± 8.9 | 22.4 ± 4.6 | N.S. | 1.48 |
| 11 | [DPhe$^{11}$, His$^{12}$]Svg$_{(11-40)}$ | 153.6 ± 33.5 | 1.4 ± 0.4 | [**] | 76.99 |
| 12 | [DPhe$^{11}$]Svg$_{(11-40)}$ | 237.3 ± 27.7 | 3.5 ± 0.2 | [*] | 47.58 |
| 13 | [DLeu$^{11}$]Svg$_{(11-40)}$ | 1670.0 ± 500.0$^a$ | 20.9 ± 4.1 | [**] | 56.07 |
| 14 | Svg$_{(11-40)}$ | 831.2 ± 668.8$^b$ | 15.4 ± 2.5 | N.S. | 37.88 |

Statistically significant differences between the K$_d$ values of the peptides:
$^a$p ≤ 0.0001 vs. 1–12, 14.
$^b$p ≤ 0.0001 vs. 1–5, 7–11, 13.
$^{c,d}$p ≤ 0.0001 vs. 2–5, 7–14.
P values of unpaired Student's t test obtained by comparing the K$_d$ value with the K$_d$ value of each peptide.
***p ≤ 0.001.
**0.01 ≥ p > 0.001.
*0.05 ≥ p > 0.01.
N.S., not significant.
$^e$Selectivity was calculated according to the equation:
Selectivity = K$_{d(rCRFR1)}$ (agonist/antagonist)/K$_{d(rCRFR1)}$ (astressin) × K$_{d(mCRFR2β)}$ (astressin)/K$_{d(mCRFR2β)}$ (agonist/antagonist).

TABLE 2

Potency of 1 μM CRF antagonist to stimulate cAMP production in transfected HEK 293 cells (% IA, intrinsic activity). Efficacy of 1 μM (rCRFR1) or 10 nM (mCRFR2β) CRF antagonist to inhibit cAMP production stimulated by oCRF (rCRFR1) or Svg (mCRFR2β) (1 nM) in transfected HEK 293 cells (relative in vitro potency).

| No. | peptides | rCRFR1 % IA | relative in vitro potency | mCRFR2β % IA | relative in vitro potency |
|---|---|---|---|---|---|
| 1 | oCRF | 1.00 | 1.00 | — | — |
| 2 | Svg | — | — | 1.00 | 1.00 |
| 3 | astressin | 0.10 ± 0.02 | 0.11 ± 0.03$^f$ | 0.004 ± 0.001 | 0.57 ± 0.04 |
| 4 | α-helical CRF$_{(9-41)}$ | 0.16 ± 0.02$^a$ | 0.58 ± 0.05 | 0.007 ± 0.004 | 0.67 ± 0.02 |
| 5 | [DPhe$^{12}$, Nle$^{21,38}$]h/rCRF$_{(12-41)}$ | 0.06 ± 0.01 | 0.33 ± 0.08$^{h,i}$ | 0.007 ± 0.002 | 0.87 ± 0.08$^i$ |
| 6 | [DPhe$^{12}$]oCRF$_{(12-41)}$ | 0.05 ± 0.01 | 0.89 ± 0.07 | 0.008 ± 0.003 | 0.92 ± 0.07$^k$ |
| 7 | [DPhe$^{11}$]rUcn$_{(11-40)}$ | 0.07 ± 0.01 | 0.18 ± 0.03$^g$ | 0.011 ± 0.003 | 0.57 ± 0.06 |
| 8 | [DPhe$^{11}$, Glu$^{12}$]rUcn$_{(11-40)}$ | 0.22 ± 0.05$^b$ | 0.42 ± 0.11 | 0.004 ± 0.001 | 0.61 ± 0.02 |
| 9 | [DLeu$^{11}$, Glu$^{12}$]rUcn$_{(11-40)}$ | 0.23 ± 0.04$^c$ | 0.56 ± 0.05 | 0.009 ± 0.002 | 0.81 ± 0.06 |
| 10 | cyclo(29-32)[DPhe$^{11}$, Glu$^{29}$, Lys$^{32}$]rUcn$_{(11-40)}$ | 0.10 ± 0.06 | 0.78 ± 0.10 | 0.005 ± 0.001 | 0.89 ± 0.01 |
| 11 | [DPhe$^{11}$, His$^{12}$]Svg$_{(11-40)}$ | 0.04 ± 0.01 | 0.73 ± 0.07 | 0.004 ± 0.001 | 0.42 ± 0.02$^{l,m}$ |
| 12 | [DPhe$^{11}$]Svg$_{(11-40)}$ | 0.07 ± 0.01 | 0.75 ± 0.13 | 0.005 ± 0.001 | 0.71 ± 0.04 |
| 13 | [DLeu$^{11}$]Svg$_{(11-40)}$ | 0.22 ± 0.04$^d$ | 0.92 ± 0.16 | 0.008 ± 0.002 | 0.75 ± 0.06 |
| 14 | Svg$_{(11-40)}$ | 0.14 ± 0.02$^e$ | 0.76 ± 0.16 | 0.005 ± 0.001 | 0.76 ± 0.02 |
|  | basal | 0.01 ± 0.003 |  | 0.004 ± 0.001 |  |

TABLE 2-continued

Potency of 1 μM CRF antagonist to stimulate cAMP production in transfected HEK 293 cells (% IA, intrinsic activity). Efficacy of 1 μM (rCRFR1) or 10 nM (mCRFR2β) CRF antagonist to inhibit cAMP production stimulated by oCRF (rCRFR1) or Svg (mCRFR2β) (1 nM) in transfected HEK 293 cells (relative in vitro potency).

| No. | peptides | rCRFR1 % IA | relative in vitro potency | mCRFR2β % IA | relative in vitro potency |
|---|---|---|---|---|---|

Statistically significant differences between the intrinsic activities of the peptides:
[a] $0.001 \geq p > 0.0001$ vs. 15.
[b,c,d] $p \leq 0.0001$ vs. 5, 6, 7, 11, 12, 15.
[e] $p \leq 0.0001$ vs. 15.

Statistically significant differences between the relative potencies of the peptides:
[f,g] $p \leq 0.0001$ vs. 6, 10–14.
[h] $0.001 \geq p > 0.0001$ vs. 6.
[i] $p \leq 0.0001$ vs. 13.
[j] $0.001 \geq p > 0.0001$ vs. 3, 7.
[k] $p \leq 0.0001$ vs. 7.
[l] $p \leq 0.0001$ vs. 5, 6, 9, 10, 13.
[m] $0.001 \geq p > 0.0001$ vs 2, 4.

TABLE 3

Binding constants ($K_d$, [nM]) of different CRF-related agonists and antagonists displacing [$^{125}$I-Try$^0$]oCRF from recombinant rCRFR1 or [$^{125}$I-Tyr$^0$]Svg from recombinant mCRFR2β.

| No. | peptides | [$^{125}$I-Tyr$^0$]oCRF $K_{d(rCRFR1)}$, [nM] | [$^{125}$I-Tyr$^0$]Svg $K_{d(mCRFR2\beta)}$, [nM] | Selectivity |
|---|---|---|---|---|
| 1 | oCRF | 0.6 ± 0.1 | 162.4 ± 37.6 | 0.002 |
| 2 | Svg | 0.7 ± 0.1 | 4.5 ± 0.6 | 0.109 |
| 3 | astressin[a] | 5.7 ± 1.6 | 4.0 ± 2.3 | 1.00 |
| 11 | [DPhe$^{11}$, His$^{12}$]Svg$_{(11-40)}$ | 153.6 ± 33.5 | 1.4 ± 0.4 | 76.99 |
| 12 | [DPhe$^{11}$]Svg$_{(11-40)}$ | 237.3 ± 27.7 | 3.5 ± 0.2 | 47.58 |
| 13 | [DLeu$^{11}$]Svg$_{(11-40)}$ | 1670.0 ± 500.0 | 20.9 ± 4.1 | 56.07 |
| 14 | Svg$_{(11-40)}$ | 831.2 ± 668.8 | 15.4 ± 2.5 | 37.88 |
| 15 | ATB-[Ala$^{32}$]astressin[b,c] | 5.3 ± 1.3 | 2.6 ± 1.0 | 1.43 |
| 16 | ATB-[Tyr$^{32}$]astressin[d] | 20.4 ± 4.6 | 38.2 ± 7.2 | 0.37 |
| 17 | ATB-[His$^{12}$]Svg$_{(12-40)}$ | 142.5 ± 22.3 | 3.1 ± 0.2 | 32.26 |
| 18 | [Tyr$^{11}$, His$^{12}$]Svg$_{(11-40)}$ | 220.9 ± 89.1 | 4.9 ± 1.8 | 31.64 |
| 19 | [Tyr$^{11}$]Svg$_{(11-40)}$ | 977.2 ± 551.0 | 20.8 ± 1.6 | 32.97 |
| 20 | [Tyr$^{12}$]Svg$_{(12-40)}$ | 995.5 ± 336.8 | 428.5 ± 118.9 | 1.63 |

[a] astressin = cyclo(30–33)[Nle$^{21,38}$, Glu$^{30}$, Lys$^{33}$]h/rCRF$_{(12-41)}$.
[b] ATB = 4-(1-azi-2,2,2-trifluoroethyl)benzoyl.
[c] [Ala$^{32}$]astressin = cyclo(30–33)[Nle$^{21,38}$, Glu$^{30}$, Ala$^{32}$, Lys$^{33}$]h/rCRF$_{(12-41)}$.
[d] [Tyr$^{32}$]astressin = cyclo(30–33)[Nle$^{21,38}$, Glu$^{30}$, Tyr$^{32}$, Lys$^{33}$]h/rCRF$_{(12-41)}$.
Selectivity was calculated according to the equation: Selectivity = $K_{d(rCRFR1)}$ (agonist/antagonist)/$K_{d(rCRFR1)}$ (astressin) × $K_{d(mCRFR2\beta)}$ (astressin)/$K_{d(mCRFR2\beta)}$ (agonist/antagonist).

TABLE 4

Potency of 1 μM CRF antagonist to stimulate cAMP production in transfected HEK 293 cells (rel. IA, relative intrinsic activity). Efficacy of 1 μM (rCRFR1) or 10 nM (mCRFR2β) CRF antagonist to inhibit cAMP production stimulated by oCRF (rCRFR1) or Svg (mCRFR2β) (1 nM) in transfected HEK 293 cells (rel. pot., relative potency).

| | | HEK-rCRFR1 cells | | HEK-mCRFR2β cells | |
|---|---|---|---|---|---|
| No. | peptides | rel. IA | rel. pot. | rel. IA | rel. pot. |
| 1 | oCRF | 1.00 | 1.00 | — | — |
| 2 | Svg | — | — | 1.00 | 1.00 |
| 3 | astressin | 0.10 ± 0.02 | 0.11 ± 0.03 | 0.004 ± 0.001 | 0.57 ± 0.04 |
| 11 | [DPhe$^{11}$, His$^{12}$]Svg$_{(11-40)}$ | 0.04 ± 0.01 | 0.73 ± 0.07 | 0.004 ± 0.001 | 0.42 ± 0.02 |
| 12 | [DPhe$^{11}$]Svg$_{(11-40)}$ | 0.07 ± 0.01 | 0.75 ± 0.13 | 0.005 ± 0.001 | 0.71 ± 0.04 |
| 13 | [DLeu$^{11}$]Svg$_{(11-40)}$ | 0.22 ± 0.04 | 0.92 ± 0.16 | 0.008 ± 0.002 | 0.75 ± 0.06 |
| 14 | Svg$_{(11-40)}$ | 0.14 ± 0.02 | 0.76 ± 0.16 | 0.005 ± 0.001 | 0.76 ± 0.02 |
| 15 | ATB-[Ala$^{32}$]astressin[b,c] | 0.10 ± 0.01 | 0.11 ± 0.05 | 0.010 ± 0.001 | 0.30 ± 0.05 |
| 16 | ATB-[Tyr$^{32}$]astressin[d] | 0.08 ± 0.01 | 0.49 ± 0.16 | 0.008 ± 0.003 | 0.68 ± 0.17 |
| 17 | ATB-[His$^{12}$]Svg$_{(12-40)}$ | 0.15 ± 0.01 | 0.54 ± 0.06 | 0.007 ± 0.002 | 0.48 ± 0.04 |
| 18 | [Tyr$^{11}$, His$^{12}$]Svg$_{(11-40)}$ | 0.03 ± 0.01 | 0.79 ± 0.07 | 0.008 ± 0.001 | 0.37 ± 0.05 |
| 19 | [Tyr$^{11}$]Svg$_{(11-40)}$ | 0.09 ± 0.01 | 0.82 ± 0.06 | 0.007 ± 0.002 | 0.67 ± 0.04 |

TABLE 4-continued

Potency of 1 μM CRF antagonist to stimulate cAMP production in transfected HEK 293 cells (rel. IA, relative intrinsic activity). Efficacy of 1 μM (rCRFR1) or 10 nM (mCRFR2β) CRF antagonist to inhibit cAMP production stimulated by oCRF (rCRFR1) or Svg (mCRFR2β) (1 nM) in transfected HEK 293 cells (rel. pot., relative potency).

|  |  | HEK-rCRFR1 cells | | HEK-mCRFR2β cells | |
| --- | --- | --- | --- | --- | --- |
| No. | peptides | rel. IA | rel. pot. | rel. IA | rel. pot. |
| 20 | [Tyr$^{12}$]Svg$_{(12-40)}$ | 0.06 ± 0.03 | 0.90 ± 0.02 | 0.006 ± 0.002 | 0.80 ± 0.04 |
|  | basal | 0.01 ± 0.003 |  | 0.004 ± 0.001 |  |

[a]astressin = cyclo(30–33)[Nle$^{21,38}$, Glu$^{30}$, Lys$^{33}$]h/rCRF$_{(12-41)}$.
[b]ATB = 4-(1-azi-2,2,2-trifluoroethyl)benzoyl.
[c][Ala$^{32}$]astressin = cyclo(30–33)[Nle$^{21,38}$, Glu$^{30}$, Ala$^{32}$, Lys$^{33}$]h/rCRF$_{(12-41)}$.
[d][Tyr$^{32}$]astressin = cyclo(30–33)[Nle$^{21,38}$, Glu$^{30}$, Tyr$^{32}$, Lys$^{33}$]h/rCRF$_{(12-41)}$.

TABLE 5

Physiocochemical data of the CRF-analogs.

| No. | peptides | RPHPLC[a] | R$_t$ [min][b] | MS (average) calcd/found[c] |
| --- | --- | --- | --- | --- |
| 1 | oCRF | 99 | 25.9 | 4671.4/4669.2 |
| 2 | Svg | 99 | 25.4 | 4600.4/4599.4 |
| 3 | astressin | 99 | 24.8 | 3564.2/3563.3 |
| 4 | α-helical CRF$_{(9-41)}$ | 97 | 26.1 | 3827.4/3826.0 |
| 5 | [DPhe$^{12}$, Nle$^{21,38}$]h/rCRF$_{(12-41)}$ | 92 | 24.4 | 3540.2/3539.1 |
| 6 | [DPhe$^{12}$]oCRF$_{(12-41)}$ | 89 | 23.0 | 3490.1/3487.6 |
| 7 | [DPhe$^{11}$]rUcn$_{(11-40)}$ | 99 | 24.5 | 3641.2/3640.8 |
| 8 | [DPhe$^{11}$, Glu$^{12}$]rUcn$_{(11-40)}$ | 99 | 25.3 | 3633.2/3629.9 |
| 9 | [DLeu$^{11}$, Glu$^{12}$]rUcn$_{(11-40)}$ | 94 | 25.1 | 3599.1/3596.4 |
| 10 | cyclo(29–32)[DPhe$^{11}$, Glu$^{29}$, Lys$^{32}$]rUcn$_{(11-40)}$ | 99 | 24.7 | 3596.1/3593.2 |
| 11 | [DPhe$^{11}$, His$^{12}$]Svg$_{(11-40)}$ | 97 | 21.6 | 3652.3/3650.3 |
| 12 | [DPhe$^{11}$]Svg$_{(11-40)}$ | 96 | 22.1 | 3644.3/3642.4 |
| 13 | [DLeu$^{11}$]Svg$_{(11-40)}$ | 98 | 22.0 | 3610.3/3608.5 |
| 14 | Svg$_{(11-40)}$ | 99 | 22.0 | 3610.3/3608.5 |

[a]Percent purity determined by RPHPLC using solvent system: A = 0.1% TFA in water, B = 80% MeCN in 0.1% TFA in water.
[b]The retention time (R$_t$) of the compounds was determined by RPHPLC. Samples were eluted with 5% B for 5 min and then with a linear gradient of 5–95% B in 30 min.
[c]The observed m/z of the average compared with the calculated [M + H]$^+$ average mass.

REFERENCES

1. Spiess, J., J. Rivier, C. Rivier, and W. Vale, *Proc. Natl. Acad. Sci. USA* 78: 65176521 (1981).
2. Vale, W., J. Spiess, C. Rivier, and J. Rivier, *Science* 213: 1394–1397, 1981
3. Vita, N., P. Laurent, S. Lefort, P. Chalon, J.-M. Lelias, M. Kaghad, G. Le Fur, D. Caput, and P. Ferrara, *FEBS Lett.* 335: 1–5, 1993
4. Chen, R., K. A. Lewis, M. H. Perrin, and W. Vale, *Proc. Natl. Acad. Sci. USA* 90: 8967–8971, 1993
5. Perrin, M. H., C. J. Donaldson, R. Chen, K. A. Lewis, and W. Vale, *Endocrinology* 133: 3058–3061, 1993
6. Chang, C.-P., R. V. Pearse II, S. O'Connell, and M. G. Rosenfeld, *Neuron* 11: 1187–1195, 1993
7. Yu, J., L. Y. Xie, and A. B. Abou-Samra, *Endocrinology* 137: 192–197, 1996
8. Dautzenberg, F. M., K. Dietrich, M. R. Palchaudhuri, and J. Spiess, *J. Neurochem.* 69: 1640–1649, 1997
9. Lovenberg, T. W., C. W. Liaw, D. E. Grigoriadis, W. Clevenger, D. T. Chalmers, E. B. De Souza, and T. Oltersdorf, *Proc. Natl. Acad. Sci. USA* 92: 836–840, 1995
10. Perrin, M., C. Donaldson, R. Chen, A. Blount, T. Berggren, L. Bilezikjian, P. Sawchenko, and W. Vale, *Proc. Natl. Acad. Sci. USA* 92: 2969–2973, 1995
11. Kishimoto, T., R. V. Pearse II, C. R. Lin, and M. G. Rosenfeld, *Proc. Natl. Acad. Sci. USA* 92: 1108–1112, 1995
12. Stenzel, P., R. Kesterson, W. Yeung, R. D. Cone, M. B. Rittenberg, and M. P. Stenzel-Poore, *Mol. Endocrinol.* 9: 637–645, 1995
13. Valdenaire, O., T. Giller, V. Breu, J. Gottowik, and G. Kilpatrick, *Biochim. Biophys. Acta* 1352: 129–132, 1997
14. Vaughan, J., C. Donaldson, J. Bittencourt, M. H. Perrin, K. Lewis, S. Sutton, R. Chan, A. V. Turnbull, D. Lovejoy, C. Rivier, J. Rivier, P. E. Sawchenko, and W. Vale, *Nature (London)* 378: 287–292, 1995
15. Behan, D. P., S. C. Heinrichs, J. C. Troncoso, X. J. Liu, C. H. Kawas, N. Ling, and E. B. De Souza, *Nature (London)* 378: 284–287, 1995
16. Rivier, J., C. Rivier, R. Galyean, A. Miranda, C. Miller, A. G. Craig, G. Yamamoto, M. Brown, and W. Vale, *J. Med. Chem.* 36: 2851–2859, 1993
17. Hernandez, J. F., W. Kornreich, C. Rivier, A. Miranda, G. Yamamoto, J. Andrews, Y. Tache, W. Vale, and J. Rivier, *J. Med. Chem.* 36: 2860–2867, 1993
18. Miranda, A., S. C. Koerber, J. Gulyas, S. L. Lahrichi, A. G. Craig, A. Corrigan, A. Hagler, C. Rivier, and J. Rivier, *J. Med. Chem.* 37: 1450–1459, 1994
19. Gulyas, J., C. Rivier, M. Perrin, S. C. Koerber, S. Sutton, A. Corrigan, S. L. Lahrichi, A. G. Craig, W. Vale, and J. Rivier, *Proc. Natl. Acad. Sci. USA* 92: 10575–10579, 1995
20. Miranda, A., S. L. Lahrichi, J. Gulyas, S. C. Koerber, A. G. Craig, A. Corrigan, C. Rivier, W. Vale, and J. Rivier, *J. Med. Chem.* 40: 3651–3658, 1997

21. Chen, C., R. Dagnino, Jr., E. B. De Souza, D. E. Grigoriades, C. O. Huang, Kjung-II Kim, Z. Liu, T. Moran, T. R. Webb, J. P. Whitten, Y. F. Xie, and J. R. McCarthy, *J. Med. Chem.* 39: 4358–4360, 1996
22. Schulz, D. W., R. S. Mansbach, J. Sprouse, J. P. Braselton, J. Collins, M. Corman, A. Dunaiskis, S. Faraci, A. W. Schmidt, T. Seeger, P. Seymour, F. D. Tingley III, E. N. Winston, Y. L. Chen, and J. Heym, *Proc. Natl. Acad. Sci. USA* 93: 10477–10482, 1996
23. Christos, T. E., and A. Arvanitis, *Expert Opinion On Therapeutic Patents* 8: 143–152, 1998
24. Baram, T. Z., D. T. Chalmers, C. Chen, Y. Koutsoukos, and E. B. De Souza, *Brain Research* 770: 89–95, 1997
25. Lundkvist, J., Z. Chai, R. Teheranian, H. Hasanvan, T. Bartfai, F. Jenck, U. Widmer, and J.-L. Moreau, *Eur. J. Pharmacol.* 309: 195–200, 1996
26. Fisher, L., C. Rivier, J. Rivier, and M. Brown, *Endocrinology* 129: 1312–1316, 1991
27. Donaldson, C. J., S. W. Sutton, M. H. Perrin, A. Z. Corrigan, K. A. Lewis, J. E. Rivier, J. M. Vaughan, and W. W Vale, *Endocrinology* 137: 2167–2170, 1996
28. Gottowik, J., V. Goetschy, S. Henriot, E. Kitas, B. Fluhman, R. G. Clerc, J. L. Moreau, F. J. Monsma, and G. J. Kilpatrick, *Neuropharmacol.* 36: 1439–1446, 1997
29. Rühmann, A., A. K. E. Köpke, F. M. Dautzenberg, and J. Spiess, *Proc. Natl. Acad. Sci. USA* 93: 10609–10613, 1996
30. Grigoriadis, D. E., X.-J. Liu, J. Vaughn, S. F. Palmer, C. D. True, W. W. Vale, N. Ling, and E. B. De Souza, *Mol. Pharmacol.* 50: 679–686, 1996
31. Liaw, C. W., D. E. Grigoriadis, M. T. Lorang, E. B. De Souza, and R. A. Maki, *Mol Endocrin* 11: 2048–2053, 1997.

What is claimed is:

1. An isolated antagonist of a ligand of the Corticotropin-Releasing Factor Receptor, type 2 (CRFR2) lacking the 8 to 10 N-terminal amino acids of native sauvagine and comprising the amino acid sequence, $Xaa_1$-$Xaa_2$-Leu—Leu-Arg-Lys-Met-Ile-Glu-Ile-Glu-Lys-Gln-Glu-Lys-Gln—Gln-Ala-Ala-Asn-Asn-Arg-Leu—Leu—Leu-Asp-Thr-Ile-$NH_2$, SEQ ID NO. 1 wherein $Xaa_1$ is a neutral amino acid, and $Xaa_2$ is a charged amino acid.

2. The isolated antagonist of claim 1 lacking the 10 N-terminal amino acids of native sauvagine.

3. The isolated antagonist of claim 1, wherein $Xaa_1$ is a hydrophobic amino acid, and $Xaa_2$ is Glu or His.

4. The isolated antagonist of claim 3, wherein $Xaa_1$ is Leu.

5. The isolated antagonist of claim 4, wherein $Xaa_2$ is Glu.

6. The isolated antagonist of claim 1, wherein $Xaa_1$ is a polar amino acid, and $Xaa_2$ is Glu or His.

7. The isolated antagonist of claim 6, wherein $Xaa_1$ is Tyr.

8. The isolated antagonist of claim 7, wherein $Xaa_2$ is His.

9. The isolated antagonist of claim 1, wherein $Xaa_1$ is in the D-configuration.

10. The isolated antagonist of claim 9, wherein $Xaa_1$, is D-Leu.

11. The isolated antagonist of claim 9, wherein $Xaa_1$ is D-Tyr.

12. The isolated antagonist of claim 9, wherein $Xaa_1$ is D-Phe.

13. A pharmaceutical composition comprising the antagonist of claim 1, and a pharmaceutically acceptable carrier and/or diluent.

14. A kit comprising
an antagonist of claim 1.

15. The antagonist of claim 1, wherein said CRFR2 is CRFR2α or CRFR2β.

16. An isolated antagonist of a ligand of the Corticotropin Releasing Factor Receptor, type 2 (CRFR2) lacking the 11 N-terminal amino acids of native sauvagine, wherein the N-terminal amino acid of said antagonist is a charged amino acid and comprising the amino acid sequence $Xaa_1$-$Xaa_2$-Leu—Leu-Arg-Lys-Met-Ile-Glu-Ile-Glu-Lys-Gln-Glu-Lys-Glu-Lys-Gln—Gln-Ala-Ala-Asn-Asn-Arg-Leu—Leu—Leu-Asp-Thr-Ile-$NH_2$, SEQ ID NO: 1 wherein $Xaa_1$ is a neutral amino acid, and $Xaa_2$ is a charged amino acid.

17. The isolated antagonist of claim 16, wherein said charged amino acid is positively charged.

18. The isolated antagonist of claim 17, wherein said charged amino acid is His.

19. The isolated antagonist of claim 16, which comprises a phenyldiazirine group coupled to the N-terminal amino acid of said antagonist.

20. The isolated antagonist of claim 19, wherein said phenyldiazirine group is a 4-(1-azi-2,2,2-trifluoroethyl) benzoyl (ATB)-group.

* * * * *

SEQUENCE LISTING

```
<160> NUMBER OF SEQ ID NOS: 6

<210> SEQ ID NO 1
<211> LENGTH: 30
<212> TYPE: PRT
<213> ORGANISM: Artificial Sequence
<220> FEATURE:
<223> OTHER INFORMATION: Synthetic oligo-peptide capable of binding to
      the corticotropin-releasing factor receptor
<220> FEATURE:
<221> NAME/KEY: MISC_FEATURE
<222> LOCATION: (1)..(1)
<223> OTHER INFORMATION: Xaa = any amino acid, unknown or other
<220> FEATURE:
<221> NAME/KEY: MISC_FEATURE
<222> LOCATION: (2)..(2)
<223> OTHER INFORMATION: Xaa = any amino acid, unknown or other

<400> SEQUENCE: 1

Xaa Xaa Leu Leu Arg Lys Met Ile Glu Ile Glu Lys Gln Glu Lys Glu
1               5                   10                  15

Lys Gln Gln Ala Ala Asn Asn Arg Leu Leu Leu Asp Thr Ile
            20                  25                  30

<210> SEQ ID NO 2
<211> LENGTH: 41
<212> TYPE: PRT
<213> ORGANISM: Artificial Sequence
<220> FEATURE:
<223> OTHER INFORMATION: Synthetic oligo-peptide based on the amino acid
      sequence of the human/rat corticotropin-releasing factor (h/rCRF)

<400> SEQUENCE: 2

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 3
<211> LENGTH: 41
<212> TYPE: PRT
<213> ORGANISM: Artificial Sequence
<220> FEATURE:
<223> OTHER INFORMATION: Synthetic oligo-peptide based on the amino acid
      sequence of the ovine corticotropin-releasing factor (oCRF)
```

```
-continued

<400> SEQUENCE: 3

Ser Gln Glu Pro Pro Ile Ser Leu Asp Leu Thr Phe His Leu Leu Arg
1               5                   10                  15

Glu Val Leu Glu Met Thr Lys Ala Asp Gln Leu Ala Gln Gln Ala His
            20                  25                  30

Ser Asn Arg Lys Leu Leu Asp Ile Ala
        35                  40

<210> SEQ ID NO 4
<211> LENGTH: 40
<212> TYPE: PRT
<213> ORGANISM: Artificial Sequence
<220> FEATURE:
<223> OTHER INFORMATION: Synthetic oligo-peptide based on the amino acid
      sequence of the rat urocortin ligand (rUcn)

<400> SEQUENCE: 4

Asp Asp Pro Pro Leu Ser Ile Asp Leu Thr Phe His Leu Leu Arg Thr
1               5                   10                  15

Ile Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 5
<211> LENGTH: 40
<212> TYPE: PRT
<213> ORGANISM: Artificial Sequence
<220> FEATURE:
<223> OTHER INFORMATION: Synthetic oligo-peptide based on the amino acid
      sequence of the sauvagine ligand (Svg)

<400> SEQUENCE: 5

Glx Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
            20                  25                  30

Asn Arg Leu Leu Leu Asp Thr Ile
        35                  40

<210> SEQ ID NO 6
<211> LENGTH: 30
<212> TYPE: PRT
<213> ORGANISM: Artificial Sequence
<220> FEATURE:
<223> OTHER INFORMATION: Synthetic oligo-peptide based on the amino acid
      sequence of the astressin corticotropin releasing factor

<400> SEQUENCE: 6

Phe His Leu Leu Arg Glu Val Leu Glu Asx Ala Arg Ala Glu Gln Leu
1               5                   10                  15

Ala Gln Glu Ala His Lys Asn Arg Lys Leu Asx Glu Ile Ile
            20                  25                  30
```